(12) United States Patent
Muramatsu et al.

(10) Patent No.: US 12,156,767 B2
(45) Date of Patent: Dec. 3, 2024

(54) ULTRASOUND DIAGNOSTIC APPARATUS, ULTRASOUND DIAGNOSTIC SYSTEM, AND RECORDING MEDIUM

(71) Applicant: Konica Minolta, Inc., Tokyo (JP)

(72) Inventors: Yuki Muramatsu, Saitama (JP); Morio Nishigaki, Fujisawa (JP)

(73) Assignee: KONICA MINOLTA, INC., Tokyo (JP)

( * ) Notice: Subject to any disclaimer, the term of this patent is extended or adjusted under 35 U.S.C. 154(b) by 105 days.

(21) Appl. No.: 18/307,085

(22) Filed: Apr. 26, 2023

(65) Prior Publication Data

US 2023/0355218 A1 Nov. 9, 2023

(30) Foreign Application Priority Data

May 6, 2022 (JP) .................. 2022-076692

(51) Int. Cl.
*A61B 8/00* (2006.01)
*A61B 8/08* (2006.01)
*A61B 34/20* (2016.01)

(52) U.S. Cl.
CPC .............. *A61B 8/56* (2013.01); *A61B 8/0841* (2013.01); *A61B 8/4472* (2013.01); *A61B 8/463* (2013.01); *A61B 34/20* (2016.02); *A61B 2034/2063* (2016.02)

(58) Field of Classification Search
CPC ....... A61B 8/56; A61B 8/0841; A61B 8/4472; A61B 8/463; A61B 34/20; A61B 2034/2063; A61B 8/4427; A61B 8/461; A61B 8/54; A61B 2017/00221;
(Continued)

(56) References Cited

U.S. PATENT DOCUMENTS 6,254,540 B1 * 7/2001 Kikuchi .............. G01S 15/8993
600/443
8,519,998 B2 * 8/2013 Hashimoto ............ A61B 8/461
345/589
(Continued)

FOREIGN PATENT DOCUMENTS

JP 2012-223352 A 11/2012
JP 2014-050648 A 3/2014

*Primary Examiner* — Sanjay Cattungal
(74) *Attorney, Agent, or Firm* — LUCAS & MERCANTI, LLP

(57) ABSTRACT

An ultrasound diagnostic apparatus wirelessly connected to a displayer includes: an image data generator that generates ultrasound image data based on a reception signal received from an ultrasound probe that transmits and receives ultrasound waves to and from a subject; and a hardware processor that wirelessly transmits the generated ultrasound image data to the displayer to display the ultrasound image data on the displayer, acquires refresh rate information of the ultrasound image data displayed on the displayer from the displayer, determines whether or not the refresh rate information is equal to or less than a first threshold value, and causes a notifier to notify of notification information indicating that display of the ultrasound image data on the displayer is poor due to deterioration of the wireless communication state when the refresh rate information is equal to or less than the first threshold value.

9 Claims, 7 Drawing Sheets

(58) Field of Classification Search
CPC ........ A61B 17/3403; A61B 2017/3413; A61B 2090/378
See application file for complete search history.

(56) References Cited

U.S. PATENT DOCUMENTS

| | | | | |
|---|---|---|---|---|
| 2005/0203417 A1* | 9/2005 | Okuno | ................ | A61B 8/5238 600/463 |
| 2006/0112033 A1* | 5/2006 | Vion | ...................... | G06N 20/00 706/16 |
| 2006/0184028 A1* | 8/2006 | Wen | ................... | G01S 15/8988 600/441 |
| 2006/0241428 A1* | 10/2006 | Kao | ....................... | A61B 8/465 600/437 |
| 2007/0014446 A1* | 1/2007 | Sumanaweera | ......... | G06T 15/08 382/128 |
| 2007/0167754 A1* | 7/2007 | Okuno | .................. | A61B 8/463 600/437 |
| 2008/0194960 A1* | 8/2008 | Randall | ................ | A61B 8/4411 600/459 |
| 2008/0194961 A1* | 8/2008 | Randall | ............... | G01S 7/52017 600/459 |
| 2008/0194962 A1* | 8/2008 | Randall | ................ | A61B 8/4411 73/40.7 |
| 2008/0194963 A1* | 8/2008 | Randall | ................... | A61B 8/00 600/459 |
| 2008/0194964 A1* | 8/2008 | Randall | ................ | A61B 8/4411 600/459 |
| 2009/0124907 A1* | 5/2009 | Bruce | .................. | A61B 5/7264 600/458 |
| 2010/0022880 A1* | 1/2010 | Sathyanarayana | .......................... | A61B 5/02007 600/443 |
| 2010/0056924 A1* | 3/2010 | Powers | ................ | A61B 8/0816 600/458 |
| 2011/0162673 A1* | 7/2011 | Samain | ................ | A45D 44/005 424/59 |
| 2012/0128218 A1* | 5/2012 | Amyot | .................... | G06T 19/00 382/128 |
| 2012/0245465 A1* | 9/2012 | Hansegard | ............. | A61B 8/466 600/443 |
| 2013/0182926 A1* | 7/2013 | Lee | ........................ | G06V 20/20 382/131 |
| 2014/0073925 A1* | 3/2014 | Kho | ........................ | A61B 8/0866 600/443 |
| 2015/0245823 A1* | 9/2015 | Jin | ........................... | A61B 8/14 600/443 |
| 2022/0125409 A1* | 4/2022 | Hattori | .................. | A61B 8/463 |
| 2022/0133281 A1* | 5/2022 | Hattori | .................. | A61B 8/463 600/440 |
| 2022/0142616 A1* | 5/2022 | Murakami | ............... | A61B 8/54 |
| 2022/0378401 A1* | 12/2022 | Heid | .................... | A61B 8/4444 |
| 2024/0315668 A1* | 9/2024 | Tsubota | ................ | A61B 8/469 |

\* cited by examiner

ULTRASOUND DIAGNOSTIC APPARATUS, ULTRASOUND DIAGNOSTIC SYSTEM, AND RECORDING MEDIUM

CROSS-REFERENCE TO RELATED APPLICATIONS

The entire disclosure of Japanese Patent Application No. 2022-076692 filed on May 6, 2022 is incorporated herein by reference in its entirety.

TECHNICAL FIELD

The present invention relates to an ultrasound diagnostic apparatus, an ultrasound diagnostic system, and a recording medium.

DESCRIPTION OF THE RELATED ART

In ultrasound diagnosis, the state of the heart or fetus is obtained as an ultrasound image with a simple operation of applying an ultrasound probe from the body surface or the body cavity of a subject, who is a patient, and the safety is high. Therefore, an examination can be performed repeatedly. An ultrasound diagnostic apparatus used to perform such an ultrasound diagnosis is known.

An ultrasound diagnostic apparatus in which wireless communication is applied to communication between components is known. In wireless communication, the real-time display of the ultrasound image may deteriorate due to a reduction in communication speed. Therefore, there is a demand to improve the real-time display of the ultrasound image.

For this reason, there is known an ultrasound diagnostic apparatus which includes an ultrasound probe, an apparatus body wirelessly connected to the ultrasound probe, and a monitor whose display is controlled by the apparatus body and in which the apparatus body monitors an index value of wireless communication and the amount of ultrasound image data transmitted from the ultrasound probe to the apparatus body is reduced when the index value becomes less than a threshold value (see JP 2014-50648 A).

In addition, there is known an ultrasound diagnostic apparatus which includes a transmission-side unit, which includes an ultrasound probe and generates ultrasound image data, and a reception-side unit, which is wirelessly connected to the transmission-side unit and receives and stores the ultrasound image data, and in which the reception-side unit generates third packet data from first packet data received during the allowed reception period instead of second packet data received during the non-allowed reception period, in which reception is not allowed due to the transmission delay caused by the line state of wireless communication, and combines the first packet data and the third packet data to generate packet data for real-time observation (see JP 2012-223352 A).

SUMMARY OF THE INVENTION

However, in the ultrasound diagnostic apparatus disclosed in JP 2014-50648 A, the data rate is reduced by reducing the scanning line density of the echo signal, which is the source of the ultrasound image data. For this reason, the image quality of all pieces of ultrasound image data displayed on the monitor is degraded. When performing simultaneous recording of the pieces of ultrasound image data displayed, the image quality of the recorded ultrasound image data is also degraded. When an operator, such as a doctor, diagnoses (examines) a subject or performs treatment on the subject while observing the degraded ultrasound image displayed on the monitor, the accuracy thereof may be reduced. In particular, when administering drug to a subject and collecting body fluids using a puncture needle, if the real-time display of the ultrasound image deteriorates or the image quality is poor, there is a risk that the puncture needle accidentally reaches tissues, such as nerves, blood vessels, and lungs, to cause injury.

In the ultrasound diagnostic apparatus disclosed in JP 2012-223352 A, unlike in the ultrasound diagnostic apparatus disclosed in JP 2014-50648 A, all the pieces of ultrasound image data are not degraded. However, since it is necessary to add a circuit or a function for performing processing, such as temporary storage of an image or image interpolation, to a display device that displays wirelessly transmitted ultrasound image data, the configuration of the apparatus becomes complicated.

It is an object of the present invention to simplify the configuration of the apparatus and to safely and accurately perform diagnosis and treatment.

To achieve at least one of the abovementioned objects, according to an aspect of the present invention, an ultrasound diagnostic apparatus reflecting one aspect of the present invention is an ultrasound diagnostic apparatus wirelessly connected to a displayer including: an image data generator that generates ultrasound image data based on a reception signal received from an ultrasound probe that transmits and receives ultrasound waves to and from a subject; and a hardware processor that wirelessly transmits the generated ultrasound image data to the displayer to display the ultrasound image data on the displayer, acquires refresh rate information of the ultrasound image data displayed on the displayer from the displayer, determines whether or not the refresh rate information is equal to or less than a first threshold value, and causes a notifier to notify of notification information indicating that display of the ultrasound image data on the displayer is poor due to deterioration of a state of the wireless communication when the refresh rate information is equal to or less than the first threshold value.

To achieve at least one of the abovementioned objects, according to an aspect of the present invention, a recording medium reflecting one aspect of the present invention is a non-transitory recording medium storing a computer readable program causing a computer of an ultrasound diagnostic apparatus wirelessly connected to a displayer to execute: generating ultrasound image data based on a reception signal received from an ultrasound probe that transmits and receives ultrasound waves to and from a subject; wirelessly transmitting the generated ultrasound image data to the displayer to display the ultrasound image data on the displayer; acquiring refresh rate information of the ultrasound image data displayed on the displayer from the displayer; determining whether or not the refresh rate information is equal to or less than a first threshold value; and causing a notifier to notify of notification information indicating that display of the ultrasound image data on the displayer is poor due to deterioration of a state of the wireless communication when the refresh rate information is equal to or less than the first threshold value.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION

Hereinafter, one or more embodiments of the present invention will be described with reference to the drawings. However, the scope of the invention is not limited to the disclosed embodiments.

First Embodiment

Figure 1:
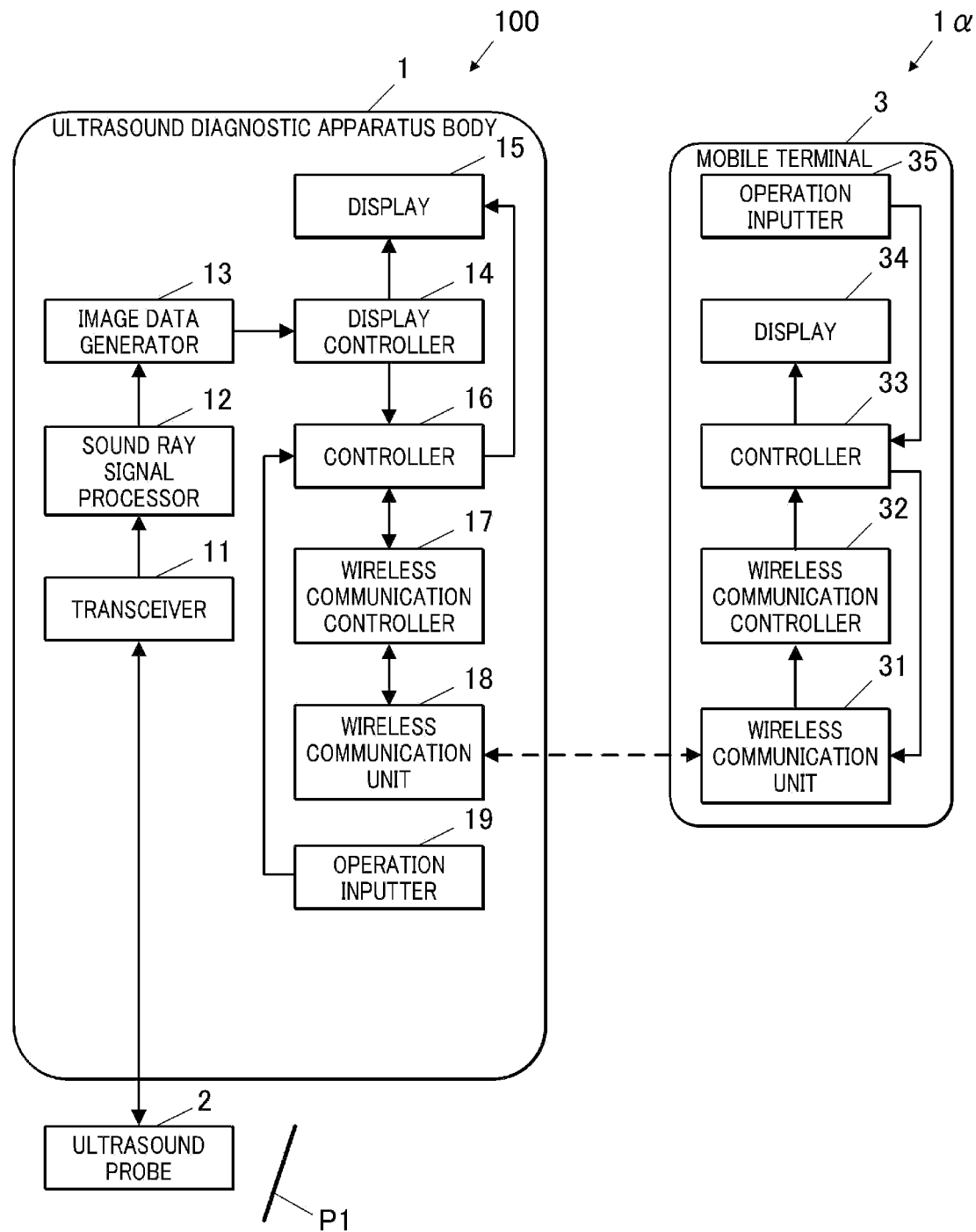
FIG. 1 is a block diagram showing the functional configuration of an ultrasound diagnostic system according to a first embodiment of the present invention.

First, the apparatus configuration of an ultrasound diagnostic system 1α according to the present embodiment will be described with reference to FIG. 1. FIG. 1 is a block diagram showing the functional configuration of the ultrasound diagnostic system 1α according to the present embodiment.

The ultrasound diagnostic system 1α according to the present embodiment is a system that is installed in a medical facility, such as a hospital, and that generates and displays ultrasound image data of a subject. As shown in FIG. 1, the ultrasound diagnostic system 1α includes an ultrasound diagnostic apparatus 100 and a mobile terminal 3. The ultrasound diagnostic apparatus 100 includes an ultrasound diagnostic apparatus body 1, an ultrasound probe 2, and a puncture needle P1. The ultrasound diagnostic apparatus 100 is a dedicated apparatus for ultrasound diagnosis that has wheels and moves on the floor of an examination room or the like, and generates and displays ultrasound image data. The mobile terminal 3 is a terminal device having at least a wireless communication function and a screen display function, such as a tablet PC (personal computer) for medical use, and is wirelessly connected to the ultrasound diagnostic apparatus 100 and displays ultrasound image data received from the ultrasound diagnostic apparatus 100.

The ultrasound probe 2 transmits ultrasound waves (transmission ultrasound waves) to a subject, such as a living body of a patient, and receives reception ultrasound waves (echoes) reflected by the subject. The ultrasound diagnostic apparatus body 1 is connected to the ultrasound probe 2. The ultrasound diagnostic apparatus body 1 causes the ultrasound probe 2 to transmit transmission ultrasound waves to the subject by transmitting a driving signal as an electrical signal to the ultrasound probe 2 and images the internal state of the subject as ultrasound image data based on a reception signal, which is an electrical signal generated by the ultrasound probe 2 in response to the reception ultrasound waves from the inside of the subject that are received by the ultrasound probe 2.

The ultrasound probe 2 has an ultrasound probe body, a cable, and a connector (all not shown in FIG. 1). The ultrasound probe body is a header portion of the ultrasound probe 2 that transmits and receives ultrasound waves. The cable is connected between the ultrasound probe body and the connector, and a driving signal for the ultrasound probe body and an ultrasound reception signal flow through the cable. The connector is a plug connector for connecting to a receptacle connector (not shown) of the ultrasound diagnostic apparatus body 1.

The ultrasound diagnostic apparatus body 1 is connected to the ultrasound probe body through the connector and the cable of the ultrasound probe 2. The ultrasound probe body includes a vibrator that is a piezoelectric element, an acoustic lens for converging transmission ultrasound waves toward a focal point, and the like. For example, a plurality of vibrators are arranged in the one-dimensional scanning direction. In the present embodiment, for example, the ultrasound probe 2 including 192 vibrators is used. The vibrators may be arranged in a two-dimensional array. The number of vibrators can be set arbitrarily. In the present embodiment, as the ultrasound probe 2, for example, a convex scanning type electronic scanning probe is adopted. However, either the electronic scanning type or the mechanical scanning type may be adopted, or any of the linear scanning type, a sector scanning system, a convex scanning system, and the like can be adopted.

The puncture needle P1 is a puncture needle for puncturing a subject for drug administration, body fluid collection, and the like. It is assumed that the puncture needle P1 is used freehand by an operator, such as a doctor. However, the puncture needle P1 is not limited to being used in this manner, and may be used in a state in which the puncture needle P1 is held by a puncture needle adapter attached to the ultrasound probe 2 (ultrasound probe body). In the present embodiment, the ultrasound diagnostic system 1α that scans the subject by using the puncture needle P1 and its operation will be described. However, the present invention can also be applied to a configuration in which a subject is scanned without using the puncture needle P1, and this is the same for other embodiments and modification examples.

The ultrasound diagnostic apparatus body 1 includes, for example, a transceiver 11, a sound ray signal processor 12, an image data generator 13, a display controller 14, a display 15, a controller 16 (a hardware processor) as a transmission controller, an acquirer, and a notification controller, a wireless communication controller 17, a wireless communication unit 18, and an operation inputter 19. The mobile terminal 3 includes, for example, a wireless communication unit 31, a wireless communication controller 32, a controller 33, a display 34, and an operation inputter 35.

The transceiver 11 is a circuit that supplies a driving signal, which is an electrical signal, to the ultrasound probe 2 so that the ultrasound probe 2 generates a transmission ultrasound wave and receives a reception signal, which is an electrical signal, from the ultrasound probe 2 under the control of the controller 16.

The sound ray signal processor 12 is a circuit that processes an analog reception signal input from the transceiver 11 to generate and output a sound ray signal (sound ray data) under the control of the controller 16. The sound ray signal processor 12 includes, for example, an amplifier, an A/D conversion circuit, and a phasing addition circuit. The amplifier is a circuit for amplifying the reception signal at a preset predetermined gain for each individual path corresponding to each vibrator. The A/D conversion circuit is a circuit for analog-digital conversion (A/D conversion) of the amplified reception signal. The phasing addition circuit is a circuit that adjusts the time phase by giving a delay time to the A/D-converted reception signal for each individual path corresponding to each vibrator and adds up (phasing addition) the time phases to generate a sound ray signal.

Under the control of the controller 16, the image data generator 13 performs envelope detection processing, logarithmic amplification, and the like on the sound ray signal input from the sound ray signal processor 12 and performs gain adjustment and the like to convert the brightness, thereby generating B (brightness)-mode image data that is tomographic image data as ultrasound image data. That is, the B-mode image data indicates the strength of the reception signal with the brightness. However, the image data generator 13 may be able to generate ultrasound image data in other image modes, particularly other tomographic image data such as color Doppler image data.

The display controller 14 controls the display of the display 15 under the control of the controller 16. The display controller 14 converts the ultrasound image data input from the image data generator 13 into an image signal by performing processing, such as coordinate conversion, on the ultrasound image data, and outputs the image signal to the display 15 to display the image signal as an ultrasound image. The display controller 14 outputs the ultrasound image data subjected to processing, such as coordinate conversion, to the controller 16 under the control of the controller 16.

As the display 15, a display device such as an LCD (liquid crystal display) or an EL (electronic luminescence) display can be applied. The display 15 displays display information, such as an ultrasound image, on the display screen according to the image signal of the ultrasound image input from the display controller 14 or the display information input from the controller 16.

The controller 16 includes, for example, a CPU (central processing unit), a ROM (read only memory), and a RAM (random access memory). By using the CPU, the controller 16 reads various processing programs such as a system program stored in the ROM and loads the processing programs to the RAM to centrally control the operation of each unit of the ultrasound diagnostic apparatus 100 according to the loaded programs. The ROM is a nonvolatile memory, such as a semiconductor, and stores a system program corresponding to the ultrasound diagnostic apparatus 100, various processing programs executable on the system program, various kinds of data, and the like. These programs are stored in the form of computer-readable program code, and the CPU sequentially executes operations according to the program code. The RAM forms a work area for temporarily storing various programs executed by the CPU and data relevant to these programs. It is assumed that the ROM stores a first ultrasound image display program for executing a first ultrasound image display process, which will be described later.

The wireless communication controller 17 performs wireless communication control of the wireless communication unit 18 under the control of the controller 16. The wireless communication unit 18 has an antenna, a modulator/demodulator, a signal processor, and the like, and transmits and receives information to and from the mobile terminal 3 (the wireless communication unit 31 of the mobile terminal 3) by using the wireless communication method of Miracast (registered trademark). Miracast is a wireless communication method using display transmission technology based on one-to-one wireless communication. For example, by wirelessly transmitting screen information from a host device (ultrasound diagnostic apparatus 100 in the present embodiment) to another display (mobile terminal 3 in the present embodiment), the display screen of the host device can be displayed on another display.

The operation inputter 19 includes, for example, various switches, buttons, a trackball, a mouse, a keyboard, and a touch pad for inputting data, such as a command for giving an instruction to start diagnosis or personal information of the subject, and outputs an operation signal to the controller 16.

The wireless communication unit 31 includes an antenna, a modulator/demodulator, a signal processor, and the like, and transmits and receives information to and from the ultrasound diagnostic apparatus 100 (the wireless communication unit 18 of the ultrasound diagnostic apparatus 100) by using the wireless communication method of Miracast. The wireless communication controller 32 performs wireless communication control of the wireless communication unit 31 under the control of the controller 33.

The controller 33 includes, for example, a CPU, a ROM, and a RAM, and reads various processing programs such as a system program stored in the ROM and loads the processing programs to the RAM to centrally control the operation of each unit of the mobile terminal 3 according to the loaded programs.

In particular, the controller 33 decodes image data of a display screen, such as an ultrasound image of the ultrasound diagnostic apparatus 100 input from the wireless communication unit 31, to generate an image signal, and outputs the generated image signal to the display 34 so that the same display information as the display screen of the ultrasound diagnostic apparatus 100 is mirroring-displayed. The controller 33 detects the refresh rate of the video data displayed on the display 34, and controls the wireless communication unit 31 to wirelessly transmit the detected refresh rate information to the ultrasound diagnostic apparatus 100 (the wireless communication unit 18 of the ultrasound diagnostic apparatus 100). The refresh rate is the value of the number of times the displayed screen is refreshed per unit time, and indicates the number of refreshes per second in units of hertz (Hz), for example. The refresh rate detected by the controller 33 is the refresh rate of video data (video streaming data) currently displaying the mirroring screen (live ultrasound image display screen) on the mobile terminal 3 in real time.

The operation inputter 35 has a touch panel integrally arranged on the display screen of the display 34, and receives a touch input from the operator and outputs the operation information to the controller 33.

Figure 2:
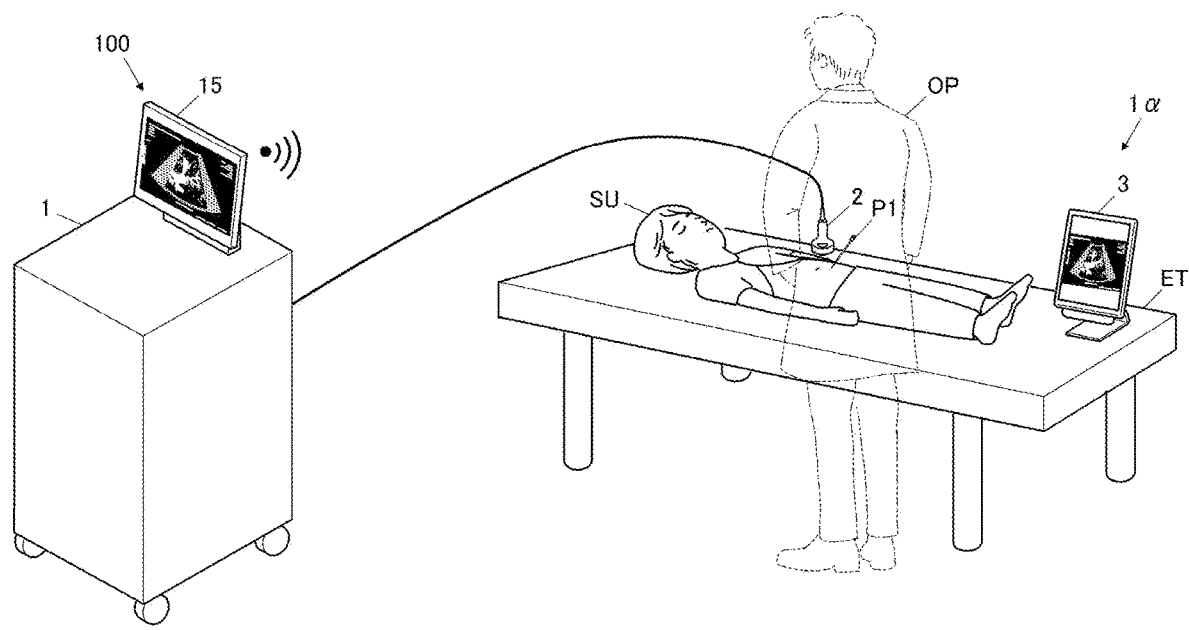
FIG. 2 is a schematic diagram showing an operator who examines a subject using the ultrasound diagnostic system.

Next, an example of a scene in which the ultrasound diagnostic system 1α is used will be described with reference to FIG. 2. FIG. 2 is a schematic diagram showing an operator OP who examines a subject SU using the ultrasound diagnostic system 1α.

As shown in FIG. 2, it is assumed that an examination table (bed) ET is installed in an examination room and the subject SU, who is a patient to be diagnosed and treated, is lying supine on the examination table ET. A case is assumed in which the operator OP, such as a doctor, punctures a target site of the subject SU with the distal end of the puncture needle P1 while observing a live ultrasound image by scanning tomograms with ultrasound waves, thereby performing drug administration, body fluid collection, and the like.

However, it is assumed that the examination room is narrow and the ultrasound diagnostic apparatus 100 cannot be moved to the back side of the examination table ET. The operator OP scans the subject SU and the puncture needle P1 using the ultrasound diagnostic apparatus 100 to generate live ultrasound image data and display the live ultrasound image data on the display 15. However, it is troublesome to always watch the display 15. For this reason, there is a risk that a position of the puncture needle P1 cannot be operated accurately or the subject SU is injured unnecessarily by the puncture needle P1. In addition, the operator OP desires to move the monitor to the opposite side of the examination table ET as viewed from the operator OP, and desires to display the monitor as close to the observation site as possible in a small examination room.

For this reason, the ultrasound diagnostic system 1α is used. Since the mobile terminal 3 that can be arranged at a desired position of the operator OP is used as a monitor, the mobile terminal 3 is arranged close to the observation site and on the opposite side of the examination table ET as viewed from the operator OP. The ultrasound diagnostic apparatus 100 wirelessly transmits ultrasound image data of the same ultrasound image as the live ultrasound image displayed on the display 15 to the mobile terminal 3 to display the ultrasound image data on the display 34. The operator OP can diagnose and treat the subject SU while observing the ultrasound images of the subject SU and the puncture needle P1 displayed on the display 34.

However, if the refresh rate of the mobile terminal 3 is reduced due to factors such as a communication failure in wireless communication between the ultrasound diagnostic apparatus 100 and the mobile terminal 3, the real-time display of the live ultrasound image on the mobile terminal 3 deteriorates. As a result, the visibility and followability of the distal end (needle tip) of the puncture needle P1 may deteriorate, or the subject SU may be injured unnecessarily by the puncture needle P1. This communication failure is, for example, speed reduction or stop of wireless communication caused by the adverse effect of electromagnetic waves from other devices in the medical facility or radio wave interference from devices using the same wireless communication band. For this reason, in the present embodiment, the operator is notified that the real-time display of the ultrasound image has deteriorated due to the first ultrasound image display process described later.

Figure 3:
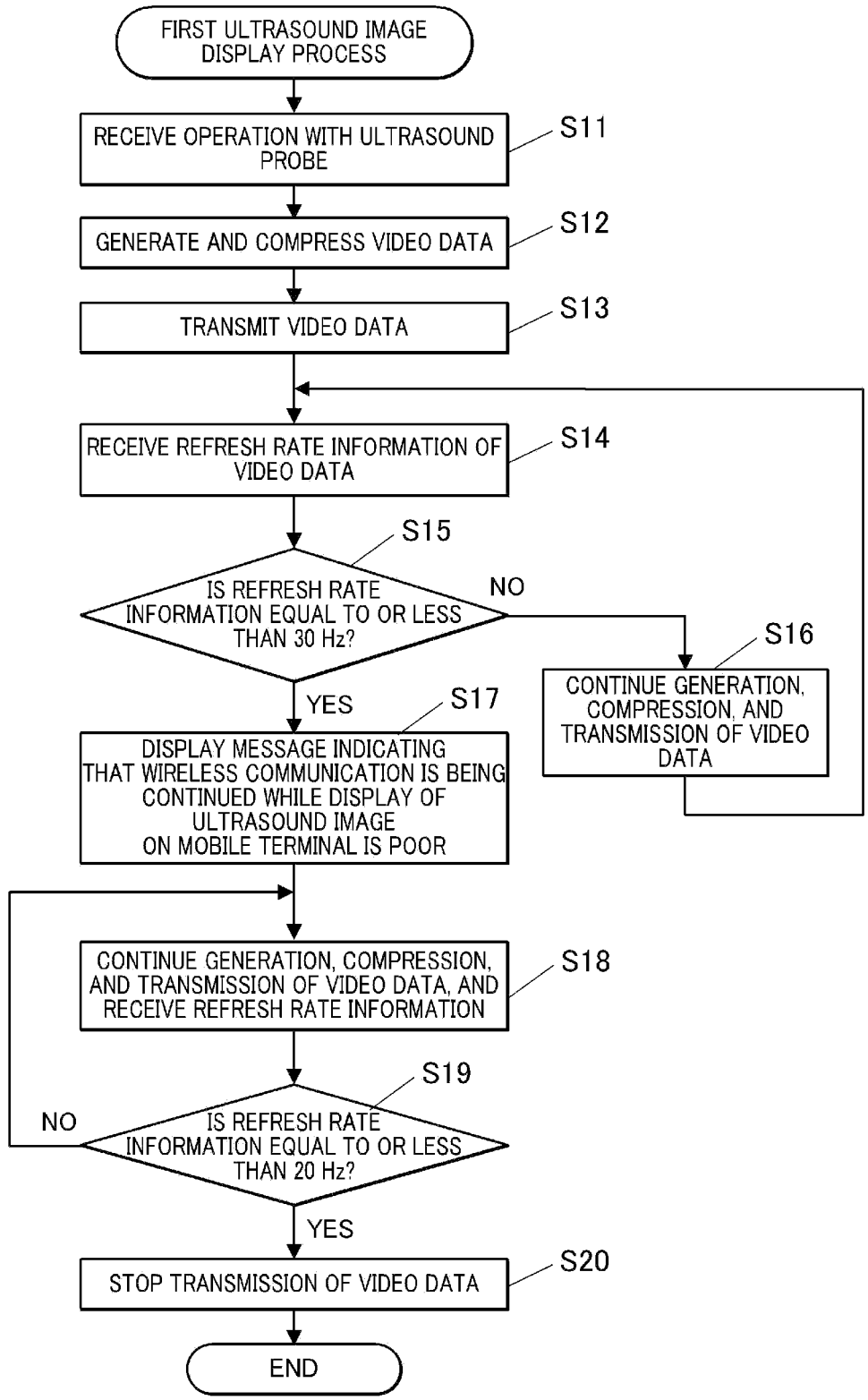
FIG. 3 is a flowchart showing a first ultrasound image display process.

Next, the first ultrasound image display process executed by the ultrasound diagnostic apparatus 100 of the ultrasound diagnostic system 1α will be described with reference to FIG. 3. FIG. 3 is a flowchart showing the first ultrasound image display process.

It is assumed that there is an operator, such as a doctor, in the examination room in advance and the subject, who is a patient to be diagnosed, enters the examination room, lies on the examination table, and waits for diagnosis and treatment using the ultrasound diagnostic system 1α. It is also assumed that the mobile terminal 3 is powered on. In the ultrasound diagnostic apparatus 100, for example, with the reception of a power-on input from the operator as a trigger, the controller 16 executes the first ultrasound image display process according to the first ultrasound image display program stored in the ROM.

As shown in FIG. 3, first, the controller 16 receives an operation to move the ultrasound probe 2 from the operator (step S11). In response to step S11, the operator places the ultrasound probe 2 on the subject, so that the subject can be freely punctured by the puncture needle P1.

Then, the controller 16 controls the transceiver 11, the sound ray signal processor 12, the image data generator 13, and the display controller 14 to generate live ultrasound image data (video data (video streaming data)) of the subject and display the live ultrasound image data on the display 15, and encodes the video data by compressing the video data using a predetermined compression method (for example, H.264/H.265) (step S12). Then, the controller 16 controls the wireless communication unit 18 through the wireless communication controller 17 to wirelessly transmit the compressed video data generated in step S12 to the mobile terminal 3 using the wireless communication method of Miracast (step S13).

In response to step S13, the controller 33 of the mobile terminal 3 controls the wireless communication unit 31 through the wireless communication controller 32 to receive the video data transmitted in step S13, decodes (reconstructs) the received data, and performs streaming display of the decoded video data (live display of the ultrasound image) on the display 34. The controller 33 detects the refresh rate of the decoded video data, and controls the wireless communication unit 31 to wirelessly transmit the detected refresh rate information to the ultrasound diagnostic apparatus 100.

Then, the controller 16 controls the wireless communication unit 18 through the wireless communication controller 17 to receive the refresh rate information transmitted from the mobile terminal 3 (step S14). Then, the controller 16 determines whether or not the refresh rate information received in step S14 is equal to or less than 30 [Hz], which is a threshold value set in advance (step S15).

If the refresh rate information is greater than 30 [Hz] (step S15; NO), the controller 16 continues the generation, encoding by compression, and transmission of the video data in steps S12 and S13 (step S16), and proceeds to step S14. If the refresh rate information is equal to or less than 30 [Hz] (step S15; YES), the controller 16 determines that the operator's diagnosis and treatment may be hindered due to the occurrence of a communication failure in wireless communication between the ultrasound diagnostic apparatus 100 and the mobile terminal 3 and the deterioration of the real-time display of the ultrasound image in the mobile terminal 3, and displays on the display 15 a message indicating that the wireless communication is being continued while the state of the ultrasound image display of the mobile terminal 3 is poor due to the deterioration of the wireless communication state (step S17).

Then, the controller 16 continues the generation, encoding by compression, and transmission of the video data in steps S12 and S13, and controls the wireless communication unit 18 through the wireless communication controller 17 to receive the refresh rate information transmitted from the mobile terminal 3 (step S18). Then, the controller 16 determines whether or not the refresh rate information received in step S18 is equal to or less than 20 [Hz] as a threshold value (<threshold value in step S15) set in advance (step S9).

If the refresh rate information is greater than 20 [Hz] (step S19; NO), the process proceeds to step S18. If the refresh rate information is equal to or less than 20 [Hz] (step S19; YES), the controller 16 stops the generation, encoding by compression, and transmission of the video data in steps S12 and S13 (step S20), thereby ending the first ultrasound image display process.

As described above, according to the present embodiment, the ultrasound diagnostic apparatus 100 is wirelessly connected to the mobile terminal 3. The ultrasound diagnostic apparatus 100 includes: the image data generator 13 that generates ultrasound image data based on a reception signal received from the ultrasound probe 2 that transmits and receives ultrasound waves to and from a subject; and the controller 16 that wirelessly transmits the generated ultrasound image data to the mobile terminal 3 to display the ultrasound image data on the mobile terminal 3, acquires the refresh rate information of the ultrasound image data displayed on the mobile terminal 3 from the mobile terminal 3, determines whether or not the refresh rate information is equal to or less than 30 [Hz] that is a first threshold value, and causes the display 15 to display a message indicating that the display of the ultrasound image data on the mobile terminal 3 is poor due to the deterioration of the wireless communication state when the refresh rate information is equal to or less than 30 [Hz].

The ultrasound diagnostic system 1α includes the ultrasound diagnostic apparatus 100 and the mobile terminal 3 that wirelessly receives ultrasound image data from the ultrasound diagnostic apparatus 100 and displays the ultrasound image data on the display 34 and wirelessly transmits the refresh rate information of the ultrasound image data to the ultrasound diagnostic apparatus 100.

Therefore, since processing such as interpolation of the ultrasound image data is not performed, the apparatus configuration can be simplified. In addition, the operator quickly notices the deterioration of the wireless communication situation by receiving a message indicating that the wireless communication is being continued while the display state of the ultrasound image data is poor. Therefore, it is possible to quickly take measures such as changing the position of the mobile terminal 3 safely in order to improve the communication situation, making a reconnection for wireless communication, switching the display destination of the ultrasound image data to a wired monitor, or referring to the display 15 of the ultrasound diagnostic apparatus 100. As a result, the operator can safely and accurately diagnose and treat the subject.

The controller 16 acquires the refresh rate information from the mobile terminal 3 even after displaying the message indicating that the wireless communication is being continued while the display state of the ultrasound image data is poor. The controller 16 determines whether or not the refresh rate information acquired after displaying the message is equal to or less than 20 [Hz], which is a second threshold value smaller than 30 [Hz], and stops wireless transmission of the ultrasound image data to the mobile terminal 3 when the refresh rate information is equal to or less than 20 [Hz]. Therefore, when diagnosis and treatment are hindered (there is a possibility of misdiagnosis and wrong treatment), the display of the ultrasound image can be safely stopped. As a result, the safety of the subject can be ensured by eliminating the risk of unnecessarily injuring the subject with the puncture needle P1.

First Modification Example

Figure 4:
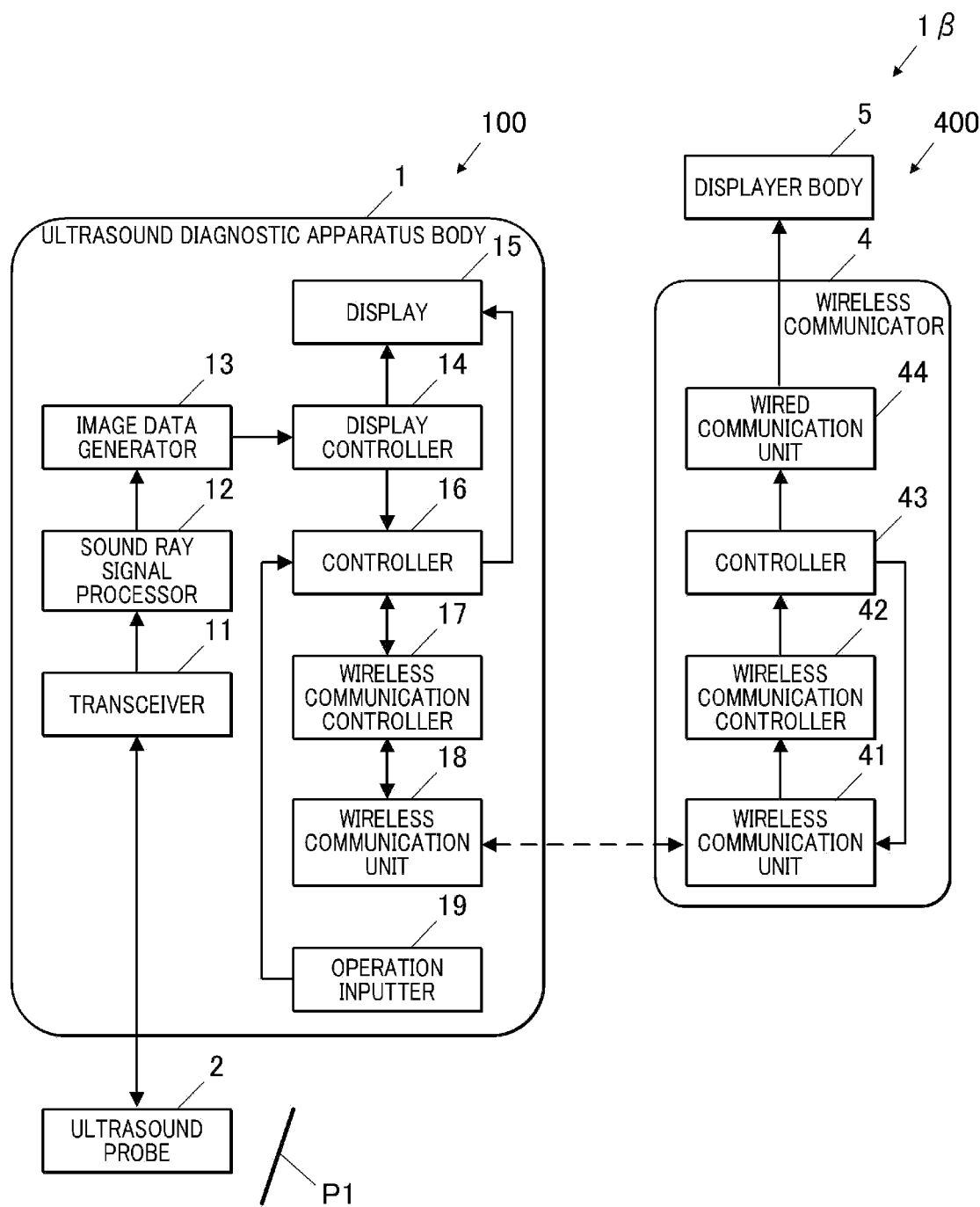
FIG. 4 is a block diagram showing the functional configuration of an ultrasound diagnostic system of a first modification example.

A first modification example as a modification example of the first embodiment will be described with reference to FIG. 4. FIG. 4 is a block diagram showing the functional configuration of an ultrasound diagnostic system 1β of this modification example.

First, the apparatus configuration of this modification example will be described with reference to FIG. 4. In this modification example, it is assumed that, instead of the ultrasound diagnostic system 1α according to the first embodiment, the ultrasound diagnostic system 1β is used as an apparatus configuration. Regarding the ultrasound diagnostic system 1β, the same parts as those of the ultrasound diagnostic system 1α are denoted by the same reference numerals, and descriptions thereof will be omitted and different parts will be mainly described.

As shown in FIG. 4, the ultrasound diagnostic system 1β includes the ultrasound diagnostic apparatus 100 and a displayer 400. The displayer 400 includes a wireless communicator 4 and a displayer body 5. The wireless communicator 4 is a relay device for wireless communication that is wired to the displayer body 5. For example, the wireless communicator 4 is a stick-shaped device that has a function for wireless communication with a wireless communication destination and is connected to the wired communication destination by wired communication. (wireless communication slave set).

The displayer body 5 is a monitor device having at least a screen display function and a wired communication connection function. As the displayer body 5, a mobile terminal, such as a tablet PC that does not have the function of generating and outputting refresh rate information as the mobile terminal 3, may be used.

The wireless communicator 4 includes, for example, a wireless communication unit 41, a wireless communication controller 42, a controller 43, and a wired communication unit 44. Similarly to the wireless communication unit 31 shown in FIG. 1, the wireless communication unit 41 transmits and receives information to and from the ultrasound diagnostic apparatus 100 (the wireless communication unit 18 of the ultrasound diagnostic apparatus 100) by using the wireless communication method of Miracast. Similarly to the wireless communication controller 32 shown in FIG. 1, the wireless communication controller 42 performs wireless communication control of the wireless communication unit 41 under the control of the controller 43.

Similarly to the controller 33 in FIG. 1, the controller 43 includes, for example, a CPU, a ROM, and a RAM, and reads various processing programs such as a system program stored in the ROM and loads the processing programs to the RAM to centrally control the operation of each unit of the wireless communicator 4 according to the loaded programs.

In particular, the controller 43 decodes video data (video streaming data) of an ultrasound image (display screen) such as an ultrasound image of the ultrasound diagnostic apparatus 100 input from the wireless communication unit 41, and outputs the generated video data to the displayer body 5 through the wired communication unit 44 so that the same display information as the display screen of the ultrasound diagnostic apparatus 100 is mirroring-displayed. The controller 43 detects the refresh rate of the video data displayed on the displayer body 5, and controls the wireless communication unit 41 to wirelessly transmit the detected refresh rate information to the ultrasound diagnostic apparatus 100 (the wireless communication unit 18 of the ultrasound diagnostic apparatus 100).

The wired communication unit 44 is wired to the displayer body 5 as an external device by using a wired communication method, such as USB (universal serial bus), and transmits and receives information to and from the displayer body 5.

The displayer body 5 includes a wired communication unit, a display panel, and a controller. The controller of the displayer body 5 displays, on the display panel, the video data of the ultrasound image received from the wireless communicator through the wired communication unit.

Next, the operation of the ultrasound diagnostic system 1β will be described. The controller 16 of the ultrasound diagnostic apparatus 100 executes the first ultrasound image display process shown in FIG. 3. In step S13, the controller 16 controls the wireless communication unit 18 through the wireless communication controller 17 to wirelessly transmit the compressed video data generated in step S12 to the wireless communicator 4 using the wireless communication method of Miracast.

In response to step S13, the controller 43 of the wireless communicator 4 controls the wireless communication unit 41 through the wireless communication controller 42 to receive the video data transmitted in step S13, decodes (reconstructs) the received data, transmits the decoded video data to the displayer body 5 through the wired communication unit 44, and performs streaming display of the decoded video data (live display of the ultrasound image). The controller 43 detects the refresh rate of the decoded video data, and controls the wireless communication unit 41 to wirelessly transmit the detected refresh rate information to the ultrasound diagnostic apparatus 100.

As described above, according to this modification example, the displayer 400 includes the displayer body 5 and the wireless communicator 4 that is wirelessly connected to the ultrasound diagnostic apparatus 100, wirelessly receives ultrasound image data from the ultrasound diagnostic apparatus 100 and displays the ultrasound image data on the displayer body 5, and transmits the refresh rate information of the ultrasound image data to the ultrasound diagnostic apparatus 100. Therefore, by connecting the wireless communicator 4 to the existing displayer body 5 by communication, the ultrasound image data can be easily displayed on the displayer body 5.

Second Embodiment

Figure 5:
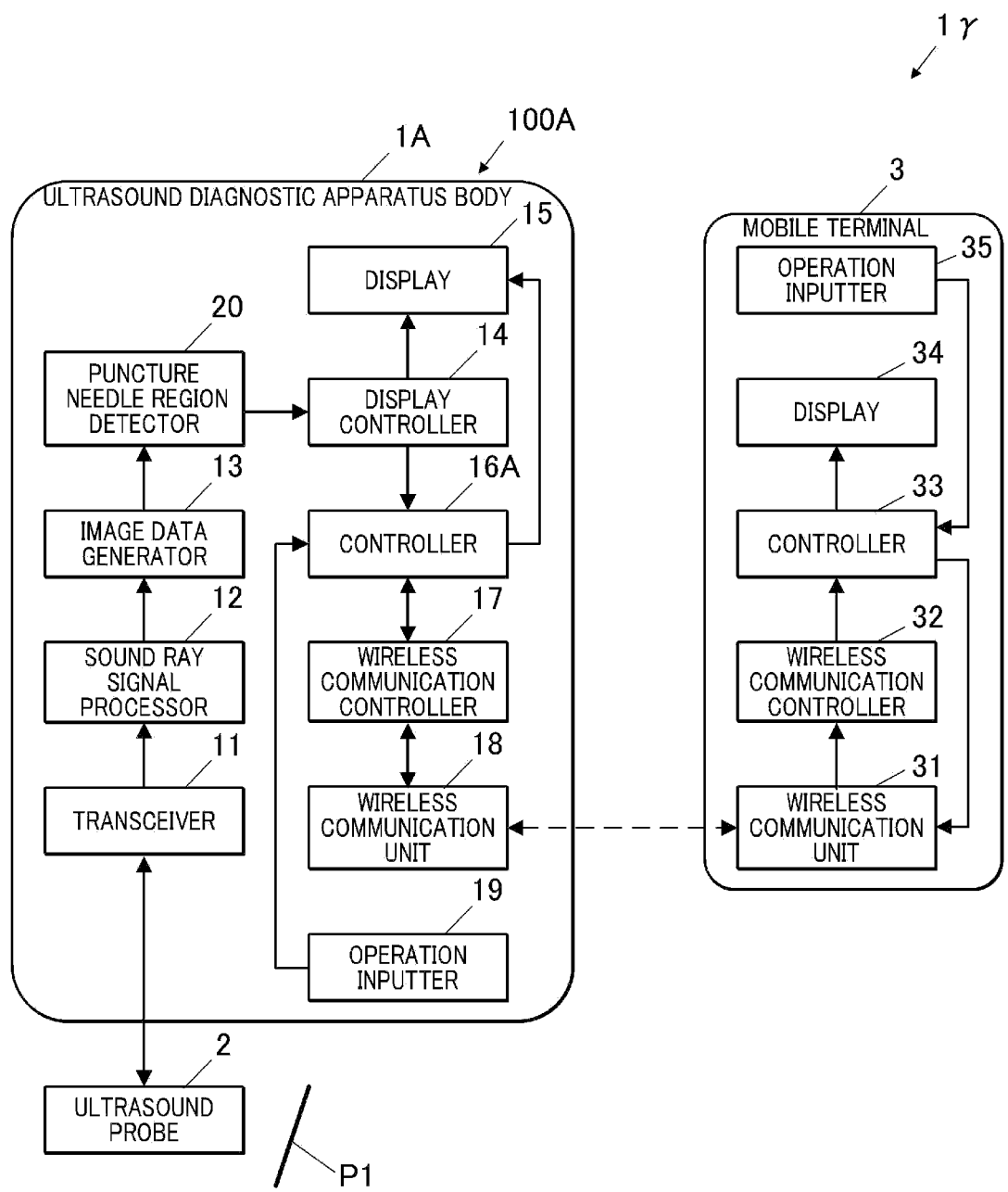
FIG. 5 is a block diagram showing the functional configuration of an ultrasound diagnostic system according to a second embodiment.
Figure 6:
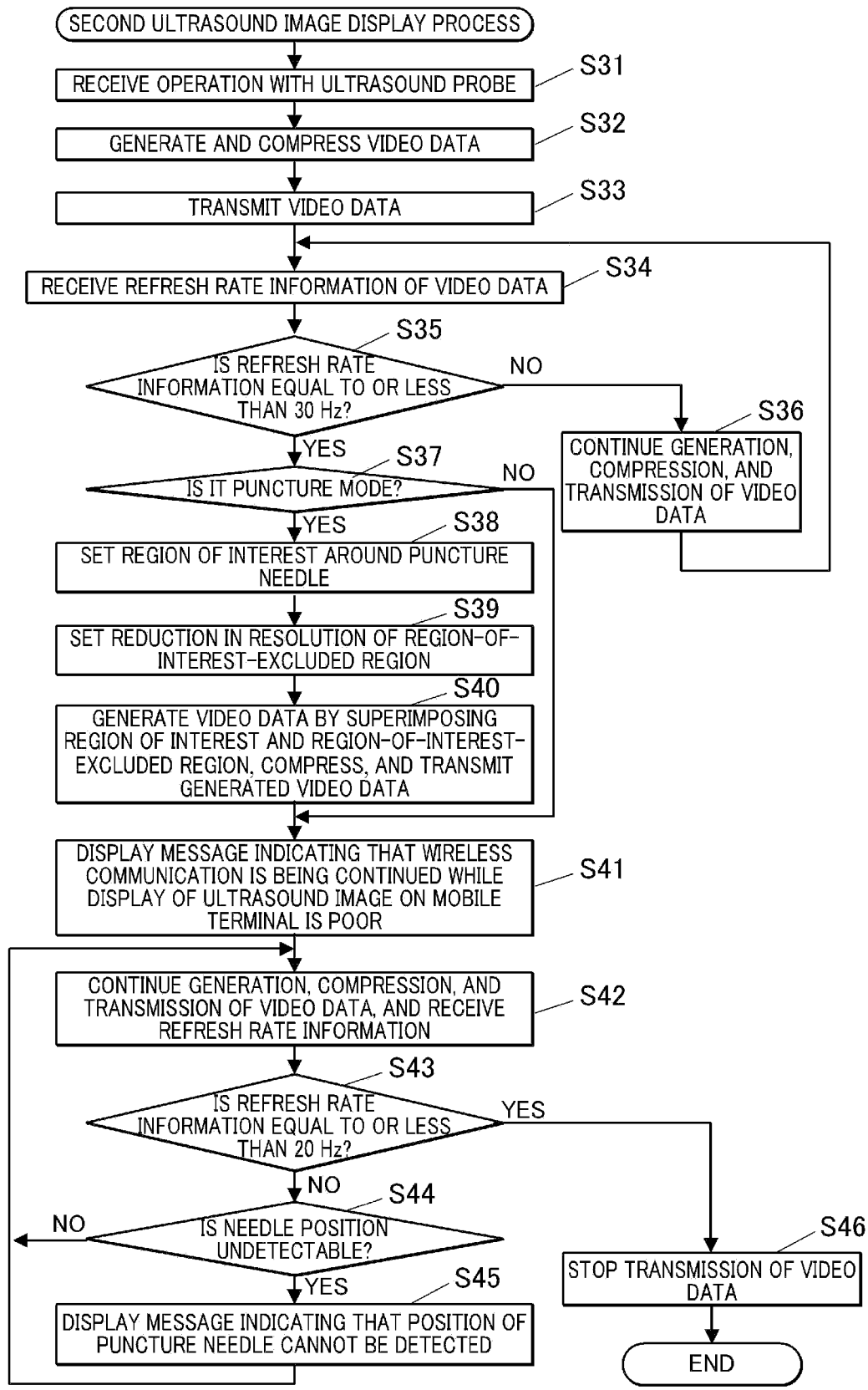
FIG. 6 is a flowchart showing a second ultrasound image display process.

A second embodiment according to the present invention will be described with reference to FIGS. 5 and 6. FIG. 5 is a block diagram showing the functional configuration of an ultrasound diagnostic system 1γ according to the present embodiment. FIG. 6 is a flowchart showing a second ultrasound image display process.

First, the apparatus configuration of the present embodiment will be described with reference to FIG. 5. In the present embodiment, it is assumed that, instead of the ultrasound diagnostic system 1α according to the first embodiment, the ultrasound diagnostic system 1γ is used as an apparatus configuration. Regarding the ultrasound diagnostic system 1γ, the same parts as those of the ultrasound diagnostic system 1α are denoted by the same reference numerals, and descriptions thereof will be omitted and different parts will be mainly described.

As shown in FIG. 5, the ultrasound diagnostic system 1γ includes an ultrasound diagnostic apparatus 100A and a mobile terminal 3. The ultrasound diagnostic apparatus 100A includes an ultrasound diagnostic apparatus body 1A, an ultrasound probe 2, and a puncture needle P1. The ultrasound diagnostic apparatus body 1A includes, for example, a transceiver 11, a sound ray signal processor 12, an image data generator 13, a display controller 14, a display 15, a controller 16A (a hardware processor), a wireless communication controller 17, a wireless communication unit 18, an operation inputter 19, and a puncture needle region detector 20.

The controller 16A has the same configuration as the controller 16 shown in FIG. 1, and centrally controls the operation of each unit of the ultrasound diagnostic apparatus 100A by using a CPU. It is assumed that the ROM of the controller 16A stores a second ultrasound image display program for executing a second ultrasound image display process, which will be described later.

Under the control of the controller 16A, the puncture needle region detector 20 outputs image data input from the image data generator 13 to the display controller 14, and detects the position of the distal end of the puncture needle P1 and a puncture needle region as its surrounding region from the ultrasound image of the input image data and outputs the position information of the detected puncture needle region in the ultrasound image to the controller 16A through the display controller 14.

As a method for detecting (identifying) the puncture needle P1 (the distal end of the puncture needle P1) from ultrasound image data, for example, as described in Japanese Patent No. 6123458, there is a method in which motion evaluation information indicating the evaluation of motion is generated by taking differences or correlations between frames from ultrasound image data of a plurality of frames, the moving speed of the distal end of the puncture needle is calculated, the position of the distal end of the puncture needle is detected from the moving speed of the distal end of the puncture needle and the motion evaluation information, and the position of the puncture needle including the distal end is identified. Alternatively, the position of the distal end of the puncture needle P1 may be estimated based on the movement history of the distal end of the puncture needle P1, the distal end may be detected based on the estimated position, and the position of the puncture needle including the distal end may be identified. Alternatively, the operator may select a contour from candidates, which are first obtained by performing contour detection, by performing an input operation on the operation inputter 19, and the position of the puncture needle P1 may be detected based on a contour similar to the selected contour.

Next, the operation of the ultrasound diagnostic system 1γ will be described with reference to FIG. 6. In the ultrasound diagnostic apparatus 100A, for example, with the reception of a power-on input from the operator and the reception of an ultrasound image display mode setting input from the operator through the operation inputter 19 as a trigger, the controller 16A executes the second ultrasound image display process according to the second ultrasound image display program stored in the ROM. It is assumed that ultrasound image display modes include a puncture mode of ultrasound image display when the puncture needle P1 is used and a normal mode of ultrasound image display when the puncture needle P1 is not used.

As shown in FIG. 6, steps S31 to S36 are the same as steps S11 to S16 of the first ultrasound image display process in FIG. 3, respectively. If the refresh rate information is equal to or less than 30 [Hz] (step S35; YES), the controller 16A determines whether or not the set ultrasound image display mode is a puncture mode (step S37). If the set ultrasound image display mode is a puncture mode (step S37; YES), the controller 16A causes the puncture needle region detector 20 to detect and acquire the position information of the puncture needle region of the ultrasound image of the video data generated by the image data generator 13, and set a region of interest around the puncture needle P1 based on the acquired position information of the puncture needle region (step S38). The region of interest is, for example, a region fixed in the center of the display screen (ultrasound image).

Then, the controller 16A performs resolution reduction setting for reducing the image quality of a region (referred to as a region-of-interest-excluded region) other than the region of interest set in step S38 in the ultrasound image of the generated video data (step S39). The degree of reduction in the resolution of the region-of-interest-excluded region in step S39 is, for example, the degree of reduction in resolution at which the data rate is halved compared with video data of an ultrasound image whose resolution is not reduced in the normal mode.

Then, based on the generated video data, the controller 16A generates video data by superimposing the ultrasound image of the region of interest set in step S38 and the ultrasound image in which the resolution of the region-of-interest-excluded region set in step S39 is reduced, encodes the video data by compressing the video data using a predetermined compression method, and controls the wireless communication unit 18 through the wireless communication controller 17 to wirelessly transmit the generated and compressed video data to the mobile terminal 3 using the wireless communication method of Miracast (step S40). In step S40 as well, the display of the video data on the display 15 in step S32 is continued. However, the present invention is not limited thereto, and video data generated by superimposing a region of interest and a region-of-interest-excluded region may be displayed on the display 15 in step S40.

Steps S41 to S43 are the same as steps S17 to S19 in FIG. 3, respectively. If the ultrasound image display mode is a normal mode (step S37; NO), the process proceeds to step S41. If the refresh rate information is greater than 20 [Hz] (step S43; NO), the controller 16A causes the puncture needle region detector 20 to detect the distal end of the puncture needle P1 in the video data generated by the image data generator 13, and determines whether or not the position of the puncture needle P1 (the distal end of the puncture needle P1) cannot be detected because the puncture needle P1 is out of the ultrasound image (or the region of interest) (step S44).

If the position of the puncture needle P1 can be detected (step S44; NO), the process proceeds to step S42. If the position of the puncture needle P1 cannot be detected (step S44; YES), the controller 16A displays a message indicating that the position of the puncture needle P1 cannot be detected on the display 15 (step S45), and proceeds to step S42. If the refresh rate information is equal to or less than 20 [Hz] (step S43; YES), step S46 is executed. Step S46 is the same as step S20 in FIG. 3.

After executing step S45, the process proceeds to S42, but the present invention is not limited thereto. For example, the process may proceed to step S46 after executing step S45, or the process may proceed to step S46 if the position of the puncture needle P1 can be detected (step S44; NO).

As described above, according to the present embodiment, when the refresh rate information is equal to or less than 30 [Hz] that is a first threshold value, the controller 16A reduces the image quality of the ultrasound image data to wirelessly transmit the ultrasound image data to the mobile terminal 3. Therefore, since the communication traffic for wireless communication is reduced by reducing the data amount of ultrasound image data, it is possible to improve the refresh rate information to improve the real-time display of the ultrasound image data.

When the refresh rate information is equal to or less than 30 [Hz], the controller 16A reduces the image quality of a region-of-interest-excluded region of the ultrasound image data to wirelessly transmit the ultrasound image data to the mobile terminal 3. Therefore, since the communication traffic for wireless communication is reduced by reducing the data amount only in the region-of-interest-excluded region other than the region of interest of the ultrasound image data, it is possible to improve the refresh rate information to improve the real-time display of the ultrasound image data, and it is possible to ensure only the image quality of the region of interest for which satisfactory real-time display is desired.

When the refresh rate information is equal to or less than 30 [Hz], the controller 16A causes the puncture needle region detector 20 to detect the position of the puncture needle P1 (the distal end of the puncture needle P1) in the ultrasound image of the ultrasound image data, sets a region of interest corresponding to the detected position of the puncture needle P1, and reduces the image quality of the region-of-interest-excluded region of the ultrasound image data to wirelessly transmit the ultrasound image data to the mobile terminal 3. Therefore, since the communication traffic for wireless communication is reduced by reducing the data amount only in the region-of-interest-excluded region other than the position of the puncture needle and the region of interest therearound in the ultrasound image data, it is possible to improve the refresh rate information to improve the real-time display of the ultrasound image data, and it is possible to ensure only the image quality of the region of interest which is required at the minimum for observing the puncture needle P1 and for which satisfactory real-time display is desired.

The controller 16A monitors the position of the puncture needle P1 in the ultrasound image data, and when the position of the puncture needle P1 cannot be detected, causes the display 15 to display a message indicating that the position of the puncture needle P1 cannot be detected. Therefore, by notifying the operator that the relative positions of the ultrasound probe 2 and the puncture needle P1 are shifted and accordingly the puncture needle P1 cannot be traced, it is possible to eliminate the risk of unnecessarily injuring the subject with the puncture needle P1.

Second Modification Example

Figure 7:
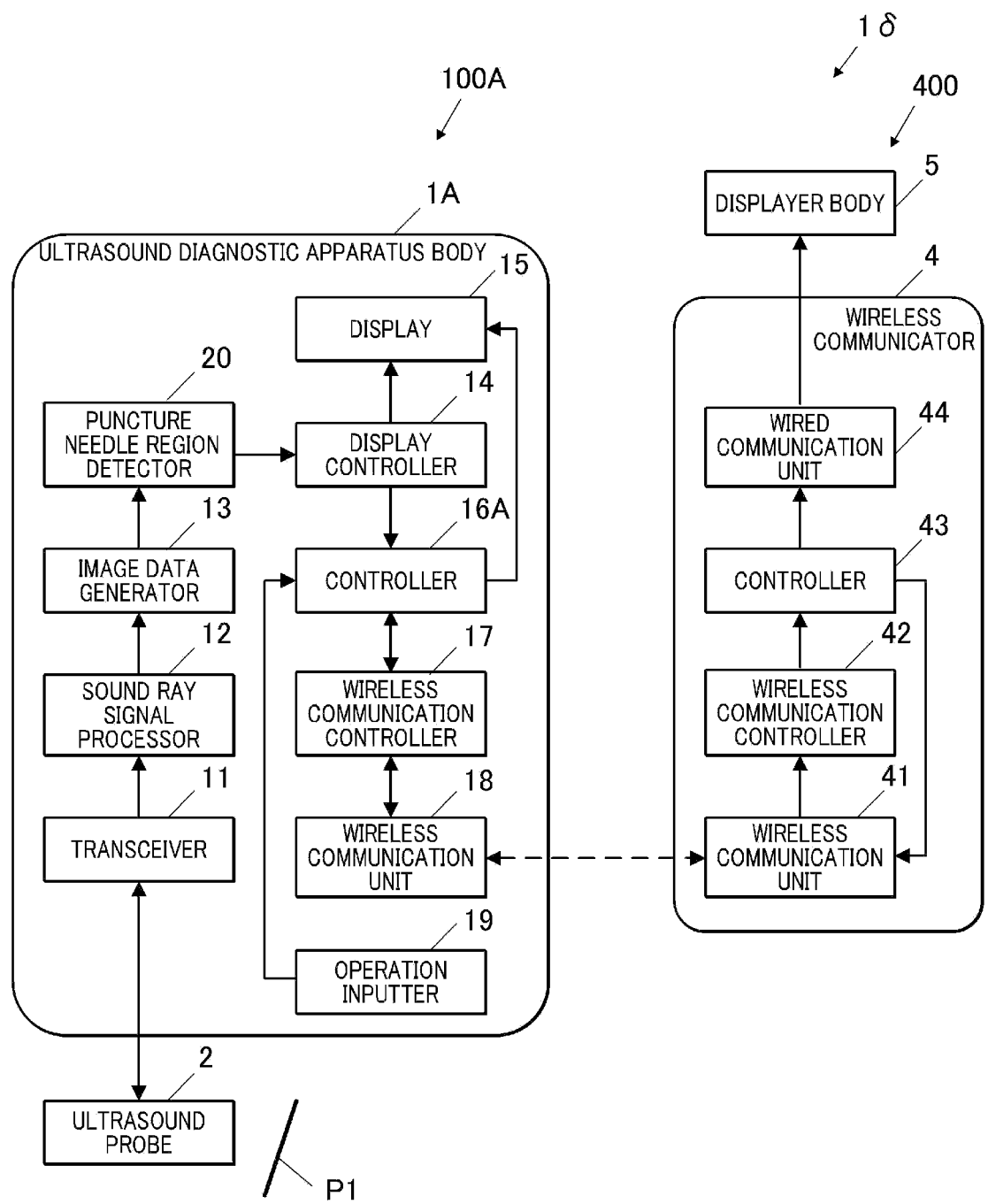
FIG. 7 is a block diagram showing the functional configuration of an ultrasound diagnostic system of a second modification example.

A second modification example as a modification example of the second embodiment will be described with reference to FIG. 7. FIG. 7 is a block diagram showing the functional configuration of an ultrasound diagnostic system 1δ of this modification example.

First, the apparatus configuration of this modification example will be described with reference to FIG. 7. In this modification example, it is assumed that, instead of the ultrasound diagnostic system 1γ according to the second embodiment, the ultrasound diagnostic system 1δ is used as an apparatus configuration. Regarding the ultrasound diagnostic system 1δ, the same parts as those of the ultrasound diagnostic system 1γ are denoted by the same reference numerals, and descriptions thereof will be omitted and different parts will be mainly described.

As shown in FIG. 7, the ultrasound diagnostic system 1δ includes the ultrasound diagnostic apparatus 100A, the wireless communicator 4, and the displayer body 5.

Next, the operation of the ultrasound diagnostic system 1δ will be described. The controller 16A of the ultrasound diagnostic apparatus 100A executes the second ultrasound image display process shown in FIG. 6. In steps S33 and S40, the controller 16A controls the wireless communication unit 18 through the wireless communication controller 17 to wirelessly transmit the generated, compressed, and encoded video data to the wireless communicator 4 using the wireless communication method of Miracast.

In response to steps S33 and S40, the controller 43 of the wireless communicator 4 controls the wireless communication unit 41 through the wireless communication controller 42 to receive the video data transmitted in steps S33 and S40, decodes (reconstructs) the received data, transmits the decoded video data to the displayer body 5 through the wired communication unit 44, and performs streaming display of the decoded video data (live display of the ultrasound image). The controller 43 detects the refresh rate of the decoded video data, and controls the wireless communication unit 41 to wirelessly transmit the detected refresh rate information to the ultrasound diagnostic apparatus 100.

As described above, according to this modification example, similar to the first modification example, the ultrasound image data can be easily displayed on the displayer body 5 by connecting the wireless communicator 4 to the existing displayer body 5 by communication.

The descriptions of the above embodiments and modification examples are examples of preferable ultrasound diagnostic apparatus, ultrasound diagnostic system, and program according to the present invention, but the present invention is not limited thereto. For example, at least two of the above embodiments and modification examples may be combined as appropriate.

In the above-described embodiments and modification examples, in step S17 of the first ultrasound image display process shown in FIG. 3 and steps S41 and S46 of the second ultrasound image display process shown in FIG. 6, each message is displayed on the display 15 for the notification of notification information, but the present invention is not limited thereto. The notification information to be displayed may be an image such as a mark or a diagram other than a message, or may be a combination of a message, an image, and the like. In addition, the display destination of the notification information is not limited to the display 15, and may be the display 34 of the mobile terminal 3, the displayer body 5, or other display devices other than the ultrasound diagnostic system, or may be a combination of at least two of the display 15, the display 34, the displayer body 5, and other display devices. As a notification information notifier other than the display, other notifiers, such as a sound outputter such as a speaker that notifies of the notification information corresponding to each message by sound or voice, a light source that provides notification by blinking or lighting patterns, and a vibrator that provides notification by vibration patterns, may be used.

In the second embodiment described above, the data amount of ultrasound image data to be wirelessly transmitted is reduced by lowering the resolution of the region-of-interest-excluded region of the ultrasound image of the ultrasound image data to reduce the image quality, but the present invention is not limited thereto. For example, as a reduction in image quality to reduce the data amount of ultrasound image data to be wirelessly transmitted, the number of colors of pixels in the region-of-interest-excluded region may be reduced (for example, the number of color gradations may be reduced, or monochrome display may be performed when the ultrasound image data is color Doppler image data).

In the above-described embodiments and modification examples, examples of using a mobile terminal as the mobile terminal 3 and the displayer 400 have been described, but the present invention is not limited thereto. As the mobile terminal 3 and the displayer 400, other display devices such as a large-screen display device for medical field education and a stationary display device may be used.

The detailed configuration and detailed operation of each unit forming the ultrasound diagnostic systems 1α, 1β, 1γ, and 1δ according to the above embodiments can be appropriately changed without departing from the spirit of the present invention.

Although embodiments of the present invention have been described and illustrated in detail, the disclosed embodiments are made for purposes of illustration and example only and not limitation. The scope of the present invention should be interpreted by terms of the appended claims

The invention claimed is:

1. An ultrasound diagnostic apparatus wirelessly connected to a displayer, comprising:
    an image data generator that generates ultrasound image data based on a reception signal received from an ultrasound probe that transmits and receives ultrasound waves to and from a subject; and
    a hardware processor that wirelessly transmits the generated ultrasound image data to the displayer to display the ultrasound image data on the displayer, acquires refresh rate information of the ultrasound image data displayed on the displayer from the displayer, determines whether or not the refresh rate information is equal to or less than a first threshold value, and causes a notifier to notify of notification information indicating that display of the ultrasound image data on the displayer is poor due to deterioration of a state of the wireless communication when the refresh rate information is equal to or less than the first threshold value.

2. The ultrasound diagnostic apparatus according to claim 1,
    wherein the hardware processor acquires the refresh rate information even after the notification of the notification information, and
    the hardware processor determines whether or not the refresh rate information acquired after the notification of the notification information is equal to or less than a second threshold value smaller than the first threshold value, and stops wireless transmission of the ultrasound image data to the displayer when the refresh rate information is equal to or less than the second threshold value.

3. The ultrasound diagnostic apparatus according to claim 1,
    wherein, when the refresh rate information is equal to or less than the first threshold value, the hardware processor reduces an image quality of the ultrasound image data to wirelessly transmit the ultrasound image data to the displayer.

4. The ultrasound diagnostic apparatus according to claim 3,
    wherein, when the refresh rate information is equal to or less than the first threshold value, the hardware processor reduces an image quality of a region excluding a region of interest of the ultrasound image data to wirelessly transmit the ultrasound image data to the displayer.

5. The ultrasound diagnostic apparatus according to claim 4,
    wherein, when the refresh rate information is equal to or less than the first threshold value, the hardware processor detects a position of a puncture needle in the ultrasound image data, sets the region of interest corresponding to the detected position of the puncture needle, and reduces an image quality of a region excluding the region of interest of the ultrasound image data to wirelessly transmit the ultrasound image data to the displayer.

6. The ultrasound diagnostic apparatus according to claim 5,
wherein the hardware processor monitors the position of the puncture needle in the ultrasound image data, and causes the notifier to notify of notification information indicating that the position of the puncture needle is not detectable when the position of the puncture needle is not detectable.

7. An ultrasound diagnostic system, comprising:
the ultrasound diagnostic apparatus according to claim 1; and
the displayer that wirelessly receives the ultrasound image data from the ultrasound diagnostic apparatus and displays the received ultrasound image data and that wirelessly transmits the refresh rate information of the ultrasound image data to the ultrasound diagnostic apparatus.

8. The ultrasound diagnostic system according to claim 7, wherein the displayer includes:
a displayer body; and
a wireless communicator that is wirelessly connected to the ultrasound diagnostic apparatus, wirelessly receives the ultrasound image data from the ultrasound diagnostic apparatus and causes the displayer body to display the received ultrasound image data, and transmits the refresh rate information of the ultrasound image data to the ultrasound diagnostic apparatus.

9. A non-transitory recording medium storing a computer readable program causing a computer of an ultrasound diagnostic apparatus wirelessly connected to a displayer to execute:
generating ultrasound image data based on a reception signal received from an ultrasound probe that transmits and receives ultrasound waves to and from a subject;
wirelessly transmitting the generated ultrasound image data to the displayer to display the ultrasound image data on the displayer;
acquiring refresh rate information of the ultrasound image data displayed on the displayer from the displayer;
determining whether or not the refresh rate information is equal to or less than a first threshold value; and
causing a notifier to notify of notification information indicating that display of the ultrasound image data on the displayer is poor due to deterioration of a state of the wireless communication when the refresh rate information is equal to or less than the first threshold value.

* * * * *